(12) United States Patent
Afriat Lauterbach et al.

(10) Patent No.: US 10,750,852 B2
(45) Date of Patent: Aug. 25, 2020

(54) BRUSHING BREATH FRESHENER

(71) Applicants: Hila Afriat Lauterbach, Ramat Gan (IL); Yaron Bar Sinai, Nahariya (IL); Alexander Gorinstein, Netanya (IL)

(72) Inventors: Hila Afriat Lauterbach, Ramat Gan (IL); Yaron Bar Sinai, Nahariya (IL); Alexander Gorinstein, Netanya (IL)

( * ) Notice: Subject to any disclaimer, the term of this patent is extended or adjusted under 35 U.S.C. 154(b) by 0 days.

(21) Appl. No.: 16/117,669

(22) Filed: Aug. 30, 2018

(65) Prior Publication Data

US 2019/0059570 A1 Feb. 28, 2019

Related U.S. Application Data

(60) Provisional application No. 62/552,409, filed on Aug. 31, 2017.

(51) Int. Cl.
| | |
|---|---|
| *A46B 5/04* | (2006.01) |
| *A46B 11/00* | (2006.01) |
| *A61Q 11/02* | (2006.01) |
| *A61K 8/30* | (2006.01) |
| *A61Q 11/00* | (2006.01) |
| *A46B 5/02* | (2006.01) |

(52) U.S. Cl.
CPC .............. *A46B 11/002* (2013.01); *A46B 5/04* (2013.01); *A46B 11/0075* (2013.01); *A61K 8/30* (2013.01); *A61Q 11/00* (2013.01); *A61Q 11/02* (2013.01); *A46B 5/02* (2013.01); *A46B 2200/1066* (2013.01)

(58) Field of Classification Search
CPC ........................................................ A46B 5/04
USPC ............................................................. 401/7, 8
See application file for complete search history.

(56) References Cited

U.S. PATENT DOCUMENTS

| | | | |
|---|---|---|---|
| 1,673,638 A | 6/1928 | Peterson | |
| 1,965,009 A | 7/1934 | Stevens | |
| 2,524,412 A | 10/1950 | Victor | |
| 4,432,114 A * | 2/1984 | Goudsmit | A46B 1/00 15/104.93 |
| 5,213,428 A * | 5/1993 | Salman | A46B 5/04 15/167.1 |
| 5,392,482 A * | 2/1995 | Drulias | A46B 5/04 15/104.94 |
| 5,440,774 A * | 8/1995 | Cole | A46B 5/04 15/105 |

(Continued)

FOREIGN PATENT DOCUMENTS

| | | |
|---|---|---|
| BE | 1007668 A3 | 9/1995 |
| CA | 2672982 A1 | 1/2011 |

(Continued)

OTHER PUBLICATIONS

PCT Search Report for corresponding International application PCT/IB2018/056645 dated Dec. 17, 2018.

*Primary Examiner* — David J Walczak
*Assistant Examiner* — Joshua R Wiljanen
(74) *Attorney, Agent, or Firm* — Heidi Brun Associates Ltd.

(57) ABSTRACT

A device for freshening breath includes a hollow housing sized to be placeable over a finger, a brush unit for brushing teeth, the brush unit being integrally formed with the housing and including a plurality of bristles; and breath freshening fluid held via surface tension within the brush unit and releasable upon of contact of the brush unit with the teeth.

12 Claims, 10 Drawing Sheets

(56) References Cited

U.S. PATENT DOCUMENTS

| | | |
|---|---|---|
| 5,819,765 A | 10/1998 | Mittiga |
| 2004/0044328 A1 | 3/2004 | Kemp |
| 2017/0367297 A1* | 12/2017 | Kim .................... A01K 13/001 |

FOREIGN PATENT DOCUMENTS

| | | |
|---|---|---|
| DE | 20112769 U1 | 6/2002 |
| DE | 202004004470 U1 | 9/2005 |
| EP | 1900302 A1 | 3/2008 |
| EP | 2459110 B1 | 9/2018 |
| FR | 2600872 A1 | 1/1988 |
| GB | 2367487 A | 4/2002 |
| WO | 2006137104 A1 | 12/2006 |

* cited by examiner

BRUSHING BREATH FRESHENER

CROSS REFERENCE TO RELATED APPLICATIONS

This application claims priority from U.S. provisional patent application 62/552,409, filed Aug. 31, 2017 which is incorporated herein by reference.

FIELD OF THE INVENTION

The present invention relates to oral hygiene generally and to breath freshness in particular.

BACKGROUND OF THE INVENTION

Oral hygiene and in particular breath freshness is an important trait in the modern world. People are very conscious of bad smelling breath and will often use an intervention in order to prevent it.

Immediate solutions for dealing with bad breath while "on the go" (during travel, before business meetings, after a meal etc.) typically include some form of flavored candy or chewing gum which help mask the smell, the use of a flavored mouthwash or similar dental hygiene product or a quick brush of the teeth using some form of portable and/or disposable toothbrush at hand together with toothpaste.

Portable and/or disposable toothbrushes exist in the art ranging from a tooth cleaner that is put on a finger and is covered with mouth detergent on one side (European Patent Publication EP19000302 published Mar. 19, 2008), a thin rubber glove that fits a finger having a sealed hollow member containing an active product that is released when the glove is rubbed against the teeth (U.S. Pat. No. 5,819,765 issued 13 Oct. 1998) and a disposable toothbrush head designed to fit on a finger which contains toothpaste concealed within the head which is released when the finger pushes down on a plate. (GB Patent Publication GB 2367487 published 10 Apr. 2002).

SUMMARY OF THE PRESENT INVENTION

There is provided, in accordance with a preferred embodiment of the present invention, a device for freshening breath, the device includes a hollow housing sized to be placeable over a finger; a brush unit for brushing teeth, the brush unit being integrally formed with the housing and including a plurality of bristles; and breath freshening fluid held via surface tension within the brush unit and releasable upon of contact of the brush unit with the teeth.

Moreover, in accordance with a preferred embodiment of the present invention, a subset of the plurality of bristles form a cavity therebetween to hold a portion of the dental fluid and where the brush unit comprises a multiplicity of the subsets.

Further, in accordance with a preferred embodiment of the present invention, the device includes a sponge to store the dental fluid.

Still further, in accordance with a preferred embodiment of the present invention, the device includes multiple bubble containers having a tangential aperture to hold the fluid.

Additionally, in accordance with a preferred embodiment of the present invention, the device includes a motorized unit to vibrate the device.

Moreover, in accordance with a preferred embodiment of the present invention, the device includes a retractable handle.

Further, in accordance with a preferred embodiment of the present invention, the cavity is at least one of: a cylindrical and conical shape.

Still further, in accordance with a preferred embodiment of the present invention, the device is reusable.

Additionally, in accordance with a preferred embodiment of the present invention, the device includes a removeable cap.

Moreover, in accordance with a preferred embodiment of the present invention, the device includes a border connecting the outer the bristles of the brush unit.

Further, in accordance with a preferred embodiment of the present invention, the housing is manufactured from at least one of: silicon, rubber, biodegradable plastic material and recyclable materials.

Still further, in accordance with a preferred embodiment of the present invention, the plurality of bristles are manufactured from at least one of silicon, rubber, biodegradable plastic material and recyclable materials.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate,

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicants have realized that the instant breath freshening solutions of the prior art are limited in that their manufacture in order to store toothpaste or other dental hygiene products may be complicated both from a production point of view and the filling/addition of the containing materials.

Applicants have further realized that any product using toothpaste also requires a water source (nearby bathroom, handy bottle of water) in order to rinse the mouth out afterwards.

Tooth brushing is also known in the art as a solution for the immediate removal of trapped food within teeth and for long term prevention of teeth related diseases such as plaque which lead to bad breath.

Applicants have also realized that the above mentioned issues of the prior art may be overcome with a brushing breath freshener that fits on the finger "thimble" like. It may have multiple bristles (like a regular tooth brush) which may be shaped and positioned accordingly to form a cavity between them. The cavity may be either cylindrical, conical or any other suitable geometrical shape. This cavity may then be filled with a low viscosity dental fluid such as a mouthwash. The dental fluid may be held in place using surface tension principles which dictate that at liquid-air interfaces, surface tension results from the greater attractions of liquid molecules to each other (due to cohesion) than the molecules in the air (due to adhesion). The resulting effect is an inward force at the surface of the liquid that causes the liquid to behave as if its surface were covered with a stretched elastic meniscus. The dental fluid may be held in place this way until the forces are disturbed (by moving the bristles). Thus the brushing breath freshener may be simple to manufacture and easy to fill with dental fluid as described in more detail herein below.

It will be appreciated that the dental fluid in question may be ingestible and cause no harm to a human being when swallowed.

Thus a user may carry the brushing breath freshener with him for use whenever he may need it and may use it to also simultaneously brush his teeth without the need of a water supply.

Figure 1:
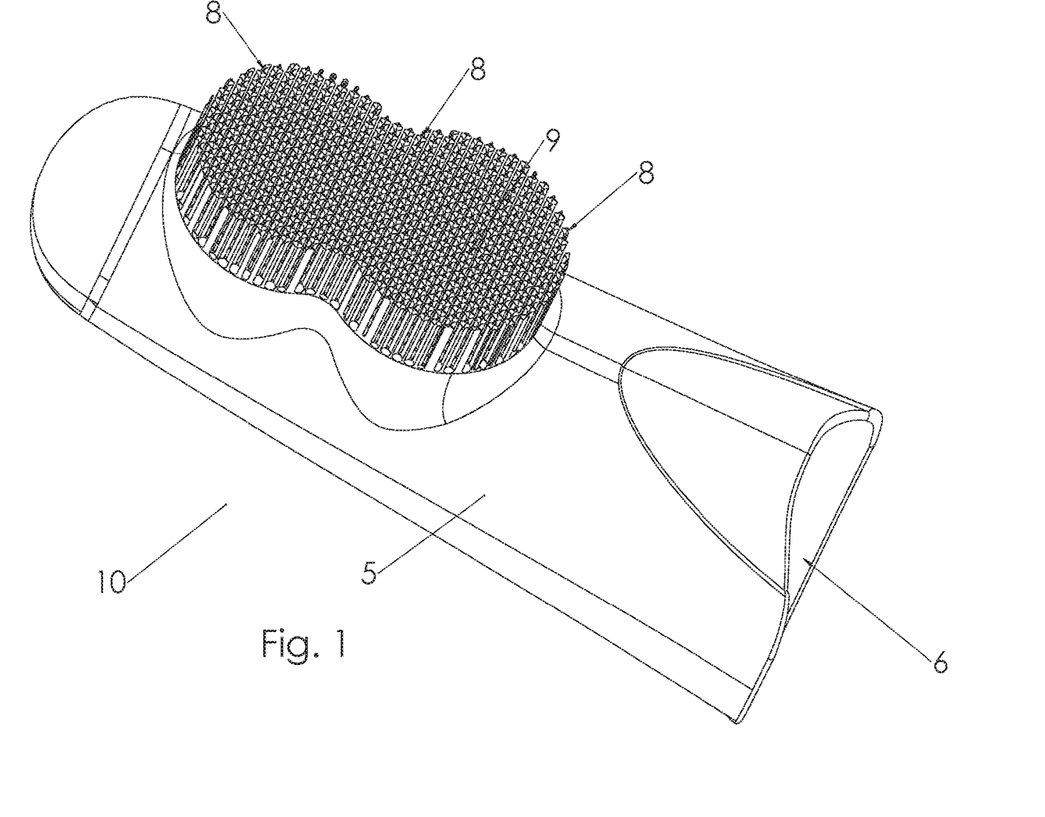
FIG. 1 is a schematic illustration of a brushing breath freshener, constructed and operative in accordance with the present invention.

Reference is now made to FIG. 1 which illustrates a brushing breath freshener 10 in accordance with an embodiment of the present invention. Brushing breath freshener 10 may comprise a housing 5 having an aperture 6. Multiple bristles 8 may be integrated with housing 5 and arranged accordingly to form a brush unit 9 as described in more detail herein below.

It will be appreciated that housing 5 may be shaped to fit comfortably over any finger via aperture 6 and may come in different sizes to fit both adults and children. It will be further appreciated that aperture 6 may be used to connect to an auxiliary unit such as a handle or a motorized unit to aid brushing as discussed in more detail herein below.

Housing 5 and bristles 8 may be manufactured using mold technology from but not limited to silicon, rubber, biodegradable plastic materials and recyclable materials suitable for human contact which may be sterilized. It will be appreciated that bristles 8 must be rigid enough to hold dental fluid without it spilling but flexible enough that when they are inserted into the mouth to brush teeth, they may be displaced enough to release the dental liquid as described in more detail herein below.

Figures 2A, 2B:
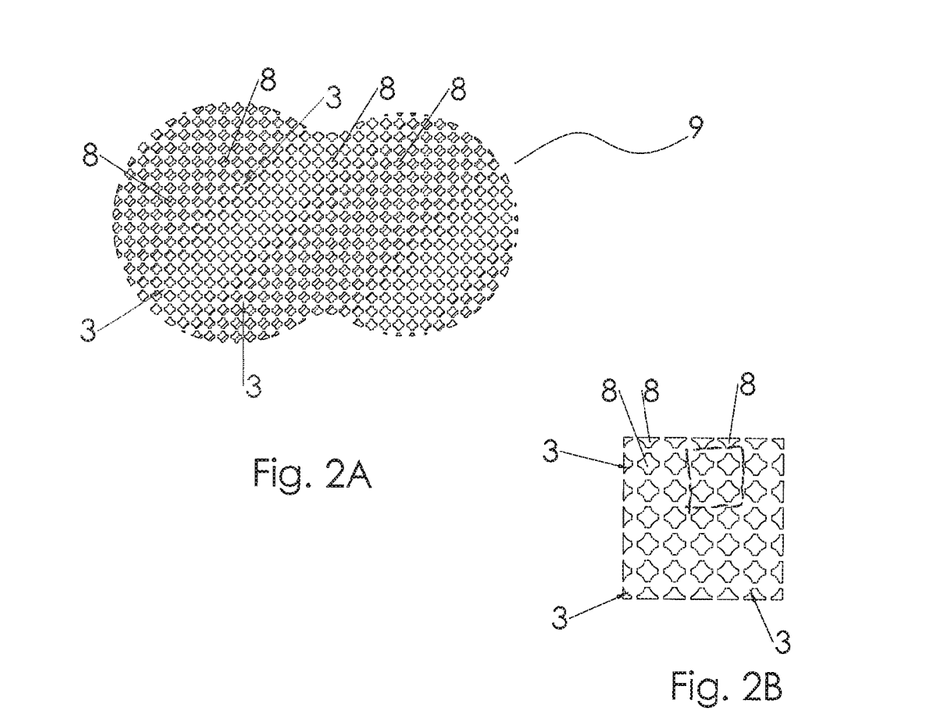
FIGS. 2A and 2B are schematic illustrations of the position and shaping of the bristles of the brushing breath freshener of FIG. 1, constructed and operative in accordance with the present invention.

Reference is now made to FIGS. 2A and 2B which illustrate the position and shaping of bristles 8. FIG. 2A illustrates the positioning of the bristles to form brush unit 9. It will be appreciated that brush unit 9 may be shaped accordingly to ensure effective tooth brushing when used. FIG. 2B is a closeup of the shape and position of bristles 8 and shows how their shape and position may form cavity 3. It will be appreciated for the sake of illustration, an embodiment of a cavity 3 is referred to with a cylindrical form that is created from 4 bristles 8. In other embodiments, less or more bristles 8 may be used to form cavity 3 depending on their shape and spacing. In other embodiments cavity 3 may be any suitable geometrical shape.

Figure 3A:
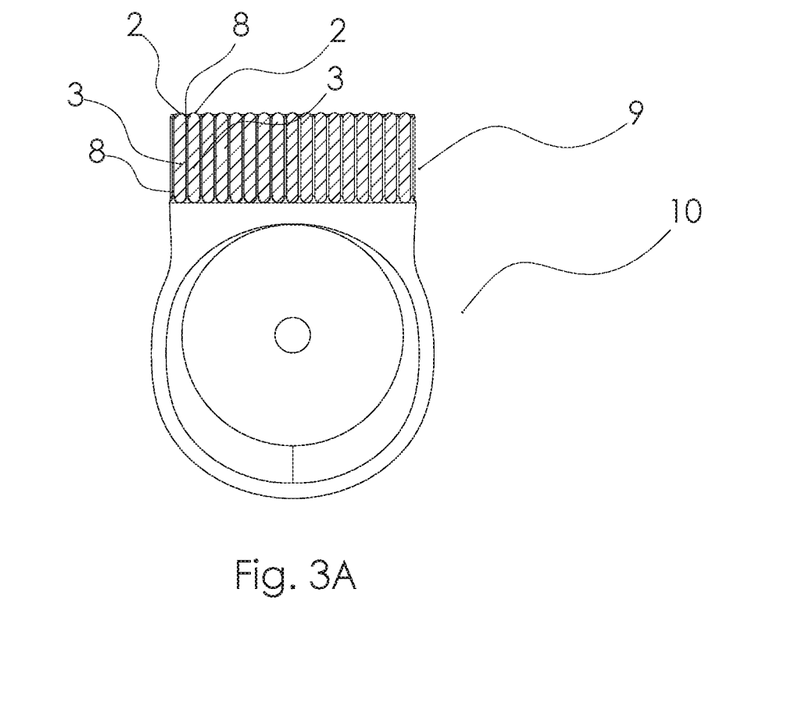
FIGS. 3A and 3B are schematic illustrations of how the bristles of FIG. 1 retain a dental fluid, constructed and operative in accordance with the present invention.
Figure 3B:
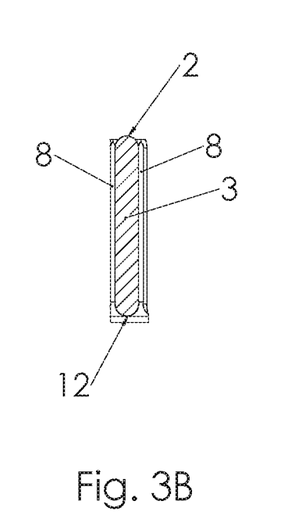

Reference is now made to FIGS. 3A and 3B which illustrate a side view of bristles 8 and the resulting cavity 3 formed between them. It will be appreciated that brushing breath freshener 10 may be dipped into a container holding a breath freshening fluid or dental fluid 12 in order to fill the multiple cavities 3. Alternatively it may be filled by a syringe or any other known industrial filling method. It will be further appreciated that the amount that may be held in each cavity 3 may be pre-determined based on the dimensions of bristles 8 and the spacing between them as well as the viscosity of dental fluid 12. As discussed herein above, due to the principles of surface tension, dental fluid 12 may fill each cavity 3 and remain in place forming a meniscus 2 until brushing breath freshener 10 is used and bristles 8 are shifted. Thus each brush unit 9 may comprise multiple cavities 3.

Thus when brushing breath freshener 10 is placed in the mouth and brush unit 9 comes into contact with another surface (such as the inside of the mouth or teeth), the movement may shift bristles 8, breaking the surface tension forces and releasing dental fluid 12 into the mouth.

It will be appreciated that the filling stage of brushing breath freshener 10 may occur during manufacture. In an alternative embodiment, brushing breath freshener 10 may be reusable and may be refilled by the user.

It will also be appreciated that dental fluid 12 may be any type of commercial mouth wash that is FDA (US Food and Drugs Administration) approved.

It will be further appreciated that the force $F_{fluidReaction}$ exerted by dental fluid 12 inside of cavity 3 may be equated to the force exerted by liquid pressure integrated over surface A of cavity 3 and should be less than $F_{surface\ tension}$ exerted due to surface tension of dental fluid 12 in order for fluid 12 to remain within cavity 3. Mathematically, this is written:

$$F_{FluidReaction} < F_{surface\ tension}. \quad \text{Equation 1}$$

The source of $F_{fluidReaction}$ is the weight of a fluid ($F_{fluid\ weight}$) and/or the fluid pressure mostly caused by gravity, $$F_{FluidReaction} = PA \quad \text{Equation 2}$$

where ρ is the pressure and A is the area over which the pressure acts.

This force can act over the surface of the fluid within cavity 13:

$$F_{FluidReaction} = F_{fluid\ weight} = PA = \rho gh\pi r^2,$$   Equation 3 where ρ is the density of fluid 12, r is the radius of the surface of cavity 3 at the liquid-air interface, h is the height of cavity 3 (e.g. of bristles 8), and g is the gravity.

Alternatively, the force $F_{FluidReaction}$ can act over a slit of height h and area s defined by the space between bristles (this is a general case ignoring cavities and slit orientations affecting the direction of the gravity):

$$\int_{A=hs} Pdhds$$   Equation 4

The force $F_{surface\ tension}$ exerted due to surface tension is:

$$F_{surface\ tension} = 2\pi r \gamma$$   Equation 5 where γ is the surface tension of fluid 12.

Using these definitions, Equation 1 at the cavity surface becomes:

$$\rho gh\pi r^2 = <2\pi r \gamma$$   Equation 6

Equation 6 can be reduced to:

$$r = 2\gamma/\rho gh$$   Equation 7

It will be appreciated that, by using Equation 7, a maximum allowable radius r may be estimated for a known bristle height of h. It will be further appreciated that the spacing of bristles may be then determined accordingly taking into account the shape and other dimensions of bristles 8 depending on the formation to be used (4 bristles 8, 3 bristles 8 etc.) in order to create cavity 3 with radius r.

It will be further appreciated that surface tension is considered a function of both the viscosity of the fluid in question and its temperature and therefore potential temperatures relating to where brushing breath freshener 10 may be stored/held may also be taken into account. Typical storage temperatures may range from 5 C-40 C. It will be further appreciated that the capability of surface tension to retain fluid is also dependent on any movement in general of brushing breath freshener 10. Thus although fluid 12 may be released when bristles 8 are displaced (as discussed herein above), it may also be displaced if brushing breath freshener 10 is subjected to low acceleration. This factor may also be taken into account when determining optimal bristle 8 spacing.

Thus for the embodiment of 4 bristles 8 (as shown in the marked area of FIG. 2B) typical dimensions may be a bristle 8 height of 5 mm, a spacing of 0.95 mm between the centers of two adjoining cylindrical cavities 3 and a spacing of 0.4 mm between two bristles 8 (this may be considered the slit width formed by s=0.4 mm and h=5 mm forming a cross section of rectangular form). Thus the resulting cavity 3 may have a radius of 0.4 mm.

Thus a user may use brushing breath freshener 10 to brush his teeth or remove any food that may be lodged between his teeth and may rinse his mouth out using dental fluid 12 before swallowing it without requiring any water.

Figure 4:
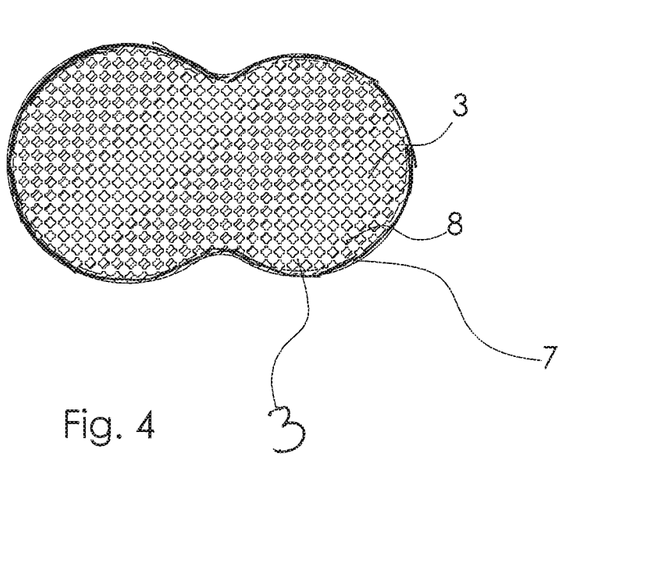
FIG. 4 is a schematic illustration of an alternative embodiment to the brushing breath freshener of FIG. 1, constructed and operative in accordance with the present invention.

In an alternative embodiment to the present invention, outer bristles 8 (of brush unit 9) may be interconnected in order to boost the holding capability of dental fluid 12. In this embodiment, brush unit 9 may contain a border 7 forming a boundary region so that the outer bristles 8 of brush unit 9 are connected to each other by a thin film of material (the same as housing 5) as is illustrated in FIG. 4 to which reference is now made.

Figure 5:
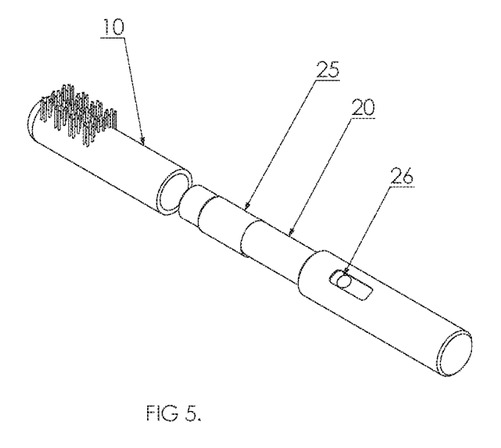
FIG. 5 is a schematic illustration of the brushing breath freshener of FIG. 1 in use with a motorized unit; constructed and operative in accordance with the present invention.
Figure 6:
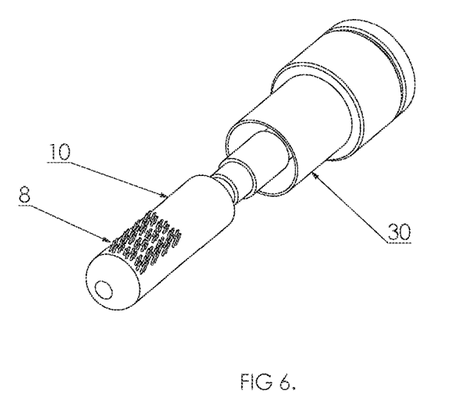
FIG. 6 is a schematic illustration of the brushing breath freshener of FIG. 1 in use with a retractable handle, constructed and operative in accordance with the present invention.

In an additional embodiment to the present invention, as discussed herein above, brushing breath freshener 10 may be connected via aperture 6 to an auxiliary unit such as a handle or a motorized unit to aid brushing. Reference is now made to FIGS. 5 and 6 which illustrate examples of such auxiliary appendages.

FIG. 5 illustrates a mechanism 20 comprising a motorized unit 25 which when connected to brushing breath freshener 10, may cause brushing breath freshener 10 to vibrate and act as an electric toothbrush. Motorized unit 25 may be activated using button 26.

FIG. 6 illustrates a mechanism 30 comprising a retractable "lipstick" like cylinder which may act as compactable handle for brushing breath freshener 10.

Figure 7:
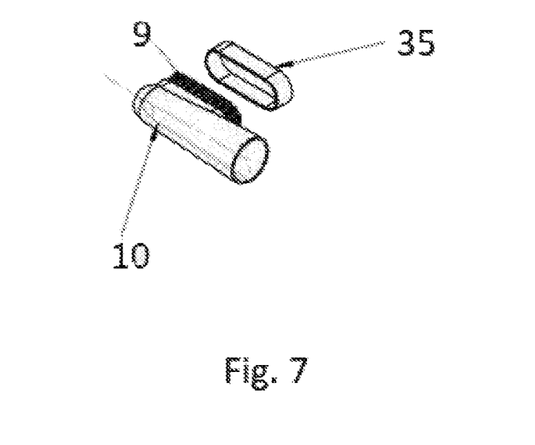
FIG. 7 is a schematic illustration of a cap for use with the brushing breath freshener of FIG. 1 constructed and operative in accordance with the present invention.

In another embodiment, brushing breath freshener 10 may have a cap or seal 35 which is shaped to snugly cover brush unit 9 containing dental liquid 12 as is illustrated in FIG. 7 to which reference is now made. Cap 35 may be manufactured from the same material as housing 5 or from any suitable edible material (such as gelatin) and may be removable. It will be appreciated that cap 35 may prevent any unnecessary movement to bristles 8 and thus prevent the release of dental fluid 12 before it is required. In an alternative embodiment, cap 35 may be part of the regular packaging of brushing breath freshener 10.

Reference is now made to FIGS. 8A-9B which illustrate alternative embodiments to the present invention.

Figure 8A:
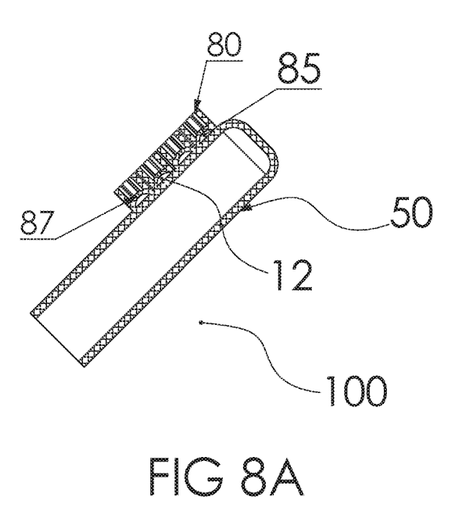
FIGS. 8A, 8B, 8C and 8D are schematic illustrations of an alternative embodiment to the brushing breath freshener of FIG. 1, constructed and operative in accordance with the present invention.
Figure 8B:
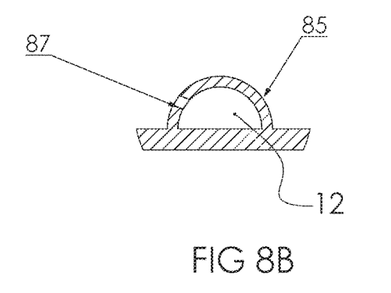
Figure 8C:
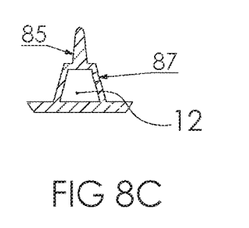
Figure 8D:
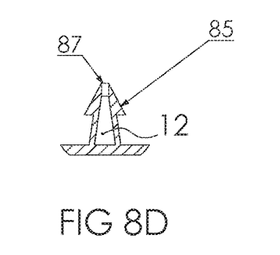

FIG. 8A illustrates a brushing breath freshener 100 having bristles 80 and bubble shaped containers 85 containing a pre-determined amount of dental liquid 12, which are integrated with housing 50 and dispersed amongst bristles 80. FIGS. 8B, 8C and 8D illustrate different embodiments of a single bubble container 85 having a tangential aperture or discharge hole 87. It will be appreciated that dental liquid 12 may remain within each bubble container 85 using similar surface tension principles as described herein above. It is only when pressure is applied to a bubble container 85 when it is in use, that the surface tension forces are broken and dental liquid 12 is released.

Figure 9A:
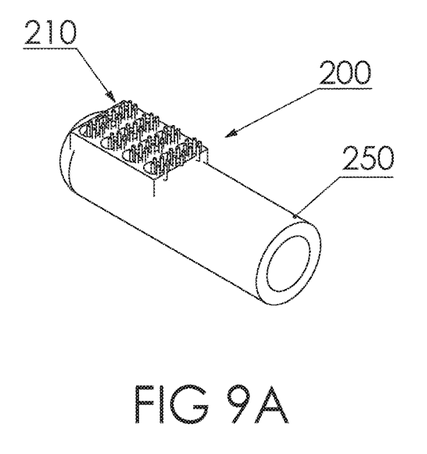
FIGS. 9A and 9B are schematic illustrations of an alternative embodiment to the brushing breath freshener of FIG. 1, constructed and operative in accordance with the present invention.
Figure 9B:
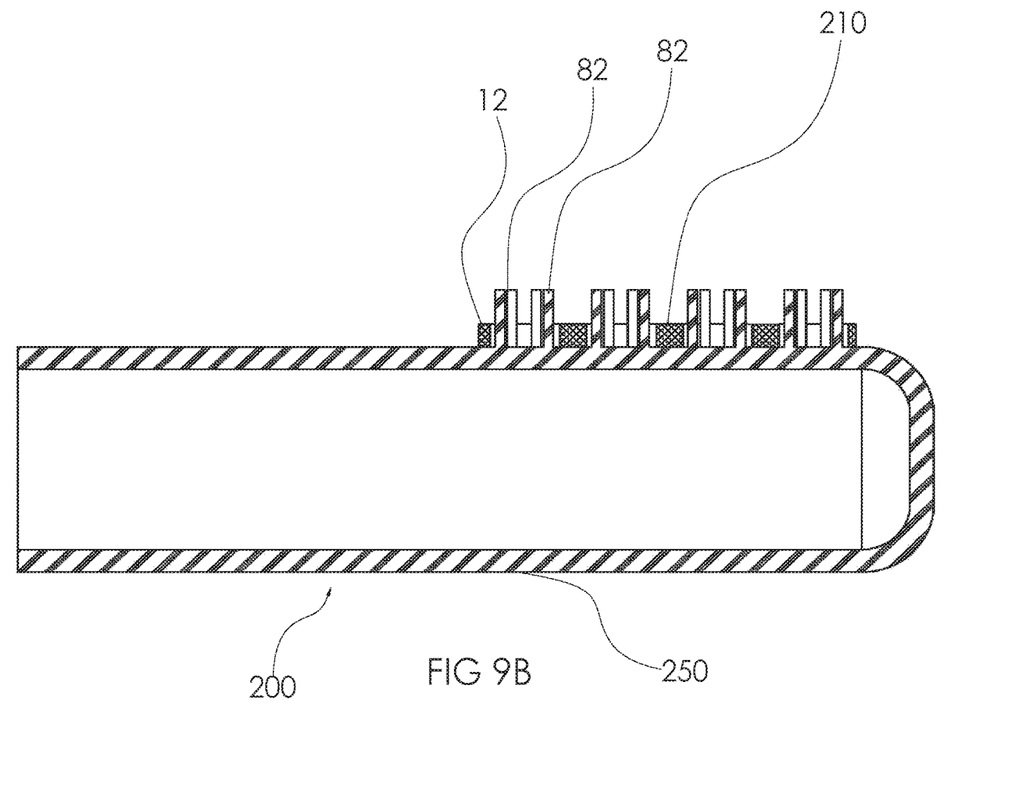

FIGS. 9A and 9B illustrate different views of a brushing breath freshener 200 comprising a sponge 210 attached to housing 250 with bristles 82. In this embodiment, sponge 210 may retain dental fluid 12 using similar surface tension principles as described herein above. Dental fluid 12 may be released when pressure is applied to sponge 210.

It will be appreciated that cap 35 may be used with all the above mentioned embodiments.

Thus by utilizing the principles of surface tension, a compact brush may retain dental fluid which may be released only when the brush is utilized for brushing teeth or being placed in the mouth in order to release a breath freshening dental fluid anytime and anyplace.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A device for freshening breath, the device comprising:
   a hollow housing sized to be placeable over a finger;
   a brush unit for brushing teeth, said brush unit being integrally formed with said housing and comprising a plurality of bristles;
   breath freshening fluid held via surface tension within said brush unit and releasable upon contact of said brush unit with said teeth; and
   multiple bubble containers having a tangential aperture to hold said fluid.

2. The device according to claim 1 and wherein a subset of said plurality of bristles form a cavity therebetween to hold a portion of said breath freshening fluid and wherein said brush unit comprises a multiplicity of said subsets.

3. The device according to claim 2 wherein said cavity is at least one of: a cylindrical and conical shape.

4. The device according to claim 2 and also comprising a removeable cap.

5. The device according to claim 2 and also comprising a border connecting the outer said bristles of said brush unit.

6. The device according to claim 1 and also comprising a sponge to store said breath freshening fluid.

7. The device according to claim 1 and also comprising a motorized unit to vibrate said device.

8. The device according to claim 1 wherein said device is reusable.

9. The device according to claim 1 and wherein said housing is manufactured from at least one of: silicon, rubber, biodegradable plastic material and recyclable materials.

10. The device according to claim 1 and wherein said plurality of bristles are manufactured from at least one of: silicon, rubber, biodegradable plastic material and recyclable materials.

11. The device according to claim 1 and also comprising a retractable handle.

12. A device for freshening breath, the device comprising:

a hollow housing sized to be placeable over a finger;

a brush unit for brushing teeth, said brush unit being integrally formed with said housing and comprising a plurality of bristles;

breath freshening fluid held via surface tension within said brush unit and releasable upon contact of said brush unit with said teeth; and a retractable handle.

* * * * *